(12) United States Patent
Willard (10) Patent No.: US 7,537,580 B2
(45) Date of Patent: May 26, 2009

(54) INTRAVASCULAR DILATATION INFUSION CATHETER

(75) Inventor: Martin R. Willard, Burnsville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 695 days.

(21) Appl. No.: 10/875,560

(22) Filed: Jun. 23, 2004

(65) Prior Publication Data
US 2005/0288632 A1 Dec. 29, 2005

(51) Int. Cl.
*A61M 29/00* (2006.01)
(52) U.S. Cl. .................................................. 604/96.01
(58) Field of Classification Search .............. 604/96.01, 604/103.01, 103.06, 103.07, 103.08, 113, 604/103.02; 606/21, 22, 23, 192, 194
See application file for complete search history.

(56) References Cited

U.S. PATENT DOCUMENTS

| | | | | |
|---|---|---|---|---|
| 4,029,104 A | | 6/1977 | Kerber et al. ................ 128/348 |
| 4,848,344 A | * | 7/1989 | Sos et al. ..................... 606/194 |
| 4,932,959 A | * | 6/1990 | Horzewski et al. ........... 606/194 |
| 5,049,132 A | * | 9/1991 | Shaffer et al. ............. 604/101.02 |
| 5,078,681 A | | 1/1992 | Kawashima et al. .......... 604/53 |
| 5,213,576 A | * | 5/1993 | Abiuso et al. ............. 604/103.01 |
| RE34,633 E | * | 6/1994 | Sos et al. ..................... 600/585 |
| 5,395,330 A | | 3/1995 | Marcadis et al. ........... 604/102.2 |
| 5,397,307 A | | 3/1995 | Goodin ................... 604/103.07 |
| 5,403,274 A | | 4/1995 | Cannon .......................... 604/9 |
| 5,421,826 A | | 6/1995 | Crocker et al. .............. 604/509 |
| 5,462,529 A | | 10/1995 | Simpson et al. .......... 604/101.04 |
| 5,571,089 A | | 11/1996 | Crocker .................. 604/103.01 |
| 5,645,529 A | | 7/1997 | Fagan et al. ............. 604/101.01 |
| 5,728,068 A | | 3/1998 | Leone et al. ............ 604/101.01 |
| 5,792,118 A | | 8/1998 | Kurth et al. .................. 604/246 |
| 5,807,330 A | | 9/1998 | Teitelbaum .............. 604/96.01 |
| 5,830,181 A | | 11/1998 | Thornton ................ 604/102.01 |
| 5,833,671 A | | 11/1998 | Macoviak et al. ........... 604/427 |
| 5,868,735 A | * | 2/1999 | Lafontaine .................... 606/21 |
| 5,968,068 A | | 10/1999 | Dehdashtian et al. ........ 606/192 |
| 5,971,979 A | * | 10/1999 | Joye et al. ...................... 606/21 |
| 6,007,517 A | | 12/1999 | Anderson ................ 604/103.04 |
| 6,048,332 A | | 4/2000 | Duffy et al. ............. 604/103.08 |
| 6,050,972 A | * | 4/2000 | Zadno-Azizi et al. ..... 604/97.01 |
| 6,056,721 A | | 5/2000 | Shulze ................... 604/101.05 |
| 6,110,191 A | | 8/2000 | Dehdashtian et al. ........ 606/192 |
| 6,117,105 A | | 9/2000 | Bresnaham et al. ....... 604/96.01 |

(Continued)

FOREIGN PATENT DOCUMENTS

EP 0564 747 10/1993

(Continued)

*Primary Examiner*—Nicholas D Lucchesi
*Assistant Examiner*—Christopher D Koharski
(74) *Attorney, Agent, or Firm*—Vidas, Arrett & Steinkraus, P.A.

(57) ABSTRACT

A medical device comprises a catheter having at least one catheter shaft, which defines an inflation lumen for transport of an inflation fluid therethrough. The inflation fluid comprises a coolant. An expandable balloon, which has a proximal cone, distal cone, and a body region therebetween, is engaged to a distal region of the at least one catheter shaft. The balloon interior is in fluid communication with the inflation lumen. A portion of the catheter distal of the balloon body defines at least one port that is in fluid communication with the inflation lumen and the balloon interior.

29 Claims, 9 Drawing Sheets

U.S. PATENT DOCUMENTS

| | | | |
|---|---|---|---|
| 6,156,005 A | 12/2000 | Theron | 604/96.01 |
| 6,379,372 B1 | 4/2002 | Dehdashtian et al. | 606/192 |
| 6,394,995 B1 | 5/2002 | Solar et al. | 604/528 |
| 6,395,023 B1 * | 5/2002 | Summers | 623/1.44 |
| 6,447,501 B1 | 9/2002 | Solar et al. | 604/528 |
| 6,547,760 B1 | 4/2003 | Samson et al. | 604/103.01 |
| 6,585,926 B1 * | 7/2003 | Mirzaee | 264/400 |
| 6,599,266 B2 | 7/2003 | Morse | 604/96.01 |
| 6,605,056 B2 | 8/2003 | Eidenschink et al. | 604/96.01 |
| 6,676,692 B2 | 1/2004 | Rabkin et al. | 623/1.11 |
| 2002/0198558 A1 | 12/2002 | Briscoe et al. | 606/192 |
| 2003/0225338 A1 | 12/2003 | Altman | 600/518 |

FOREIGN PATENT DOCUMENTS

| | | |
|---|---|---|
| WO | WO 94/21320 | 9/1994 |

* cited by examiner

INTRAVASCULAR DILATATION INFUSION CATHETER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to medical devices such as catheters and catheter assemblies for use in medical procedures. More specifically, this invention relates to catheter systems, such as the kind used in percutaneous transluminal coronary angioplasty (PTCA) procedures, as well as the kind used in cryoplasty and/or cooling procedures.

2. Description of the Related Art

Percutaneous transluminal coronary angioplasty (PTCA) is a procedure which is well established for the treatment of blockages, lesions, stenosis, thrombus, etc. present in body lumens such as the coronary arteries and/or other vessels.

A widely used form of percutaneous coronary angioplasty makes use of a dilatation balloon catheter which is introduced into and advanced through a lumen or body vessel until the distal end thereof is at a desired location in the vasculature. Once in position across a afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

It is known that in some angioplasty procedures, the reopening of a vessel is in whole or in-part frustrated by complete or partial reclosure of the artery or vessel. Often the mechanism responsible for the closure of the vessel is vessel recoil and/or more commonly restenosis of the lesion resulting from continued growth of the lesion back into the vessel.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

In some cases, where the vessel and/or surrounding tissue has had its blood flow blocked or reduced, it has been shown that by cooling the tissue the amount of necrosis is reduced if re-profusion is established within a given treatment window. However current catheter systems do not adequately provide both a mechanism for establishing re-profusion and providing a cooling effect within the desired window.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a balloon catheter that utilizes the inflation lumen and balloon to dilate lesions and infuse fluid into the blood vessel or body lumen to reduce the temperature of the tissues at or around the lesion site. In some embodiments the catheter is configured to allow the inflation media to exit the device distal of the balloon while maintaining inflation pressure of the balloon.

In at least one embodiment the inflation media is characterized as an infusate or coolant which has a temperature of less than about 37 degrees Celsius. In at least one embodiment the coolant has a temperature of about 33 degrees Celsius to about 37 degrees Celsius.

In at least one embodiment the balloon comprises a plurality of coolant ports or openings in the distal cone region of the balloon. The ports are constructed and arranged to allow the balloon during inflation to build pressure while allowing a sufficient outflow of infusate to adequately cool the surrounding tissue.

In at least one embodiment the infusate has a viscosity less than that of blood. In some embodiments the infusate comprises a solution of one or more fluids such as saline, Ringer Lactate solution etc.

In at least one embodiment, coolant ports are configured to allow the infusate to exit the balloon under pressure but prevent or restrict the flow of bodily fluids into the balloon during deflation.

In at least one embodiment the catheter comprises a valve mechanism or other occluding device within the balloon. The valve mechanism configured to allow the coolant ports to be selectively occluded or opened to allow the balloon to expand and fluid to pass through the ports when desired. In some embodiments the valve mechanism has an actuatable bellows configuration.

In at least one embodiment the catheter comprises a baffle member. The baffle member defines a plurality of baffle openings offset in position from the coolant ports. In some embodiments the baffle member is positioned within the balloon proximally adjacent the coolant ports. In some embodiments the baffle member is positioned external to the balloon, distal of the coolant ports.

In some embodiments a medical device comprises a balloon catheter wherein the inner shaft distal of the balloon is provided with at least one coolant exit port. The guidewire lumen defined by the inner shaft is in fluid communication with the balloon to permit the inflation fluid/coolant to flow from the balloon, through the inner shaft and into the guidewire lumen, and out the distal coolant exit port or ports. In at least one embodiment the catheter comprises a fluid static valve to control and/or prevent pressure loss of the coolant out the proximal end of the guidewire lumen.

In at least one embodiment the coolant may enter the guidewire lumen while the guidewire is positioned therein. In some embodiment the guidewire comprises a spring tip wire having coils through which the coolant may flow.

In at least one embodiment the guidewire lumen has one or more coolant entrance ports positioned within the balloon. In some embodiments the coolant is free to flow into the guidewire lumen via the entrance port(s) when the guidewire is withdrawn proximal of the entrance port. Flow of the coolant through the guidewire lumen and out the exit port(s) may be controlled by selectively moving the guidewire to block and/or open the entrance and/or exit ports.

In at least one embodiment the catheter is provided with one or more valve mechanisms to control the direction of the coolant flow through the port(s). In at least one embodiment the valve mechanism is positioned inside the guidewire lumen to allow coolant to flow outward from the catheter but prevents backflow of fluid during deflation of the balloon.

In at least one embodiment the catheter avoids the use of the traditional inner shaft and outer shaft configuration by mounting the balloon directly to a single shaft which defines a dual inflation/guidewire lumen. The shaft comprises one or more fluid static valves to prevent fluid and pressure loss out the proximal and/or distal ends of the catheter.

In some embodiments the balloon is a porous balloon such as the TRANSPORT™ balloon. In some embodiments the catheter comprises a multi-lumen balloon such as the CHANNEL™ balloon to provide the catheter with separate inflation and infusion lumens. The ports may be provided to such balloons to provide for proper infusion characteristics and for transmission of the coolant through the distal end.

In at least one embodiment the infusion lumen is disposed about the balloon, but which is expandable therewith.

In some embodiments the catheter is configured to allow body fluids such as blood to perfuse through the balloon when expanded. As such, the balloon may be provided with one or more ports of channels therethrough for the transmission of bodily fluid through the balloon when in the expanded state.

In some embodiments the catheter may be configured for the delivery of one or more therapeutic agents. In at least one embodiments a therapeutic agent is included with the infusate.

In some embodiments the catheter may be utilized to deploy a stent or other expandable prosthesis.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
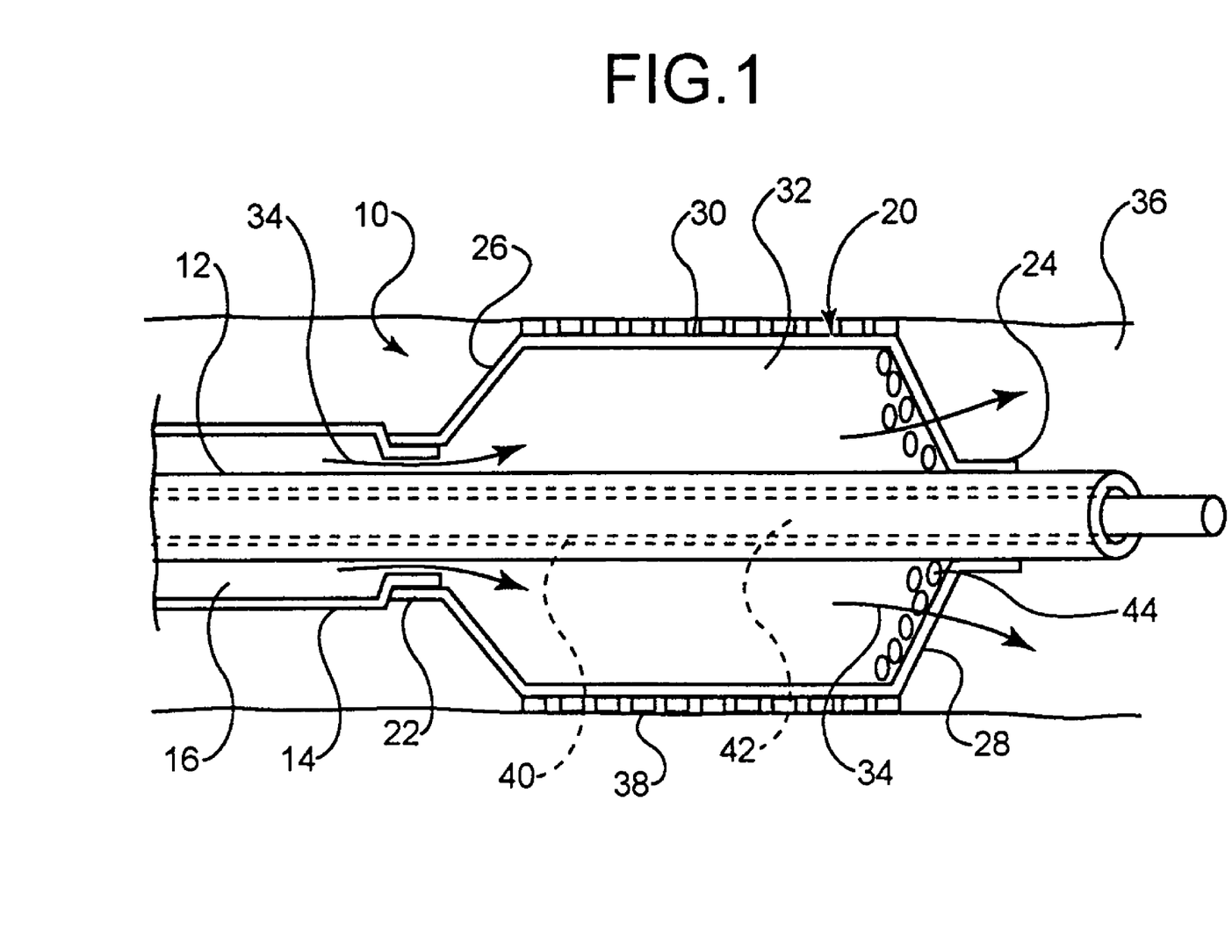
FIG. 1 is a partial cross-sectional side view of an embodiment of the invention.

In at least one embodiment, an example of which is shown in FIG. 1, the invention is directed to a medical device comprising a catheter 10. The catheter 10 comprises an inner shaft 12 and outer shaft 14 and a balloon 20. The outer shaft 14 is disposed about a portion of the inner shaft 12. The radially adjacent portions of the shafts 12 and 14 define a lumen 16 therebetween.

The balloon 20 includes a proximal waist 22, a distal waist 24, a proximal cone 26, a distal cone 28 and a working or body portion 30 therebetween. When mounted on the catheter 10 the proximal waist 22 of the balloon 20 is engaged to a portion of the outer shaft 14 and the distal waist 24 is engaged to a portion of the inner shaft 12. As a result of this configuration the interior 32 of the balloon 20 is in fluid communication with the lumen 16. By transmitting an inflation fluid, indicated by arrow 34, under pressure through the lumen 16, the balloon 20 may be expanded from a collapsed and/or folded reduced diameter configuration to an expanded greater diameter configuration within a body lumen or vessel 36, such as is shown.

The catheter 10, may be a push catheter, over-the-wire catheter, MONORAIL™ catheter, rapid exchange catheter or other type of catheter desired. In the embodiment depicted in FIG. 1, the inner shaft 12 defines a second lumen or guidewire lumen 40, through which a guidewire 42 is passed. The catheter 10 may then be advanced along the guidewire 42 to a predetermined location in the vessel 36.

In some embodiments an expandable endoprosthesis such as a stent 38 may be disposed about the balloon, such that when the balloon 20 is expanded the stent is also expanded for delivery into the vessel 36.

As used herein the term 'stent' refers to an expandable prosthesis for implantation into a body lumen or vessel and includes devices such as stents, grafts, stent-grafts, vena cava filters, etc. In some embodiments a stent may be at least partially constructed of any of a variety of materials such as stainless steel, nickel, titanium, nitinol, platinum, gold, chrome, cobalt, as well as any other metals and their combinations or alloys. In some embodiments a stent may be at least partially constructed of a polymer material. In some embodiments a stent may be at least partially constructed of a shape-memory polymer or material. In some embodiments a stent may be balloon expandable, self-expandable, hybrid expandable or a combination thereof In some embodiments a stent or other portions of the catheter may include one or more radiopaque members. In some embodiments a stent may include one or more therapeutic and/or lubricious coatings applied thereto.

In the embodiment shown in FIG. 1, the distal cone 28 of the balloon 20 defines one or more openings 44 through which the inflation fluid 34 may be allowed to pass from the interior 32 of the balloon 20 out into the vessel 36 distal of the balloon. While the openings 44 are configured to allow the inflation fluid 34 to pass out of the balloon interior they restrict such outflow to an extent sufficient to allow the balloon 20 to build pressure and expand to its expanded configuration despite the loss of fluid 34 through the openings 44. Openings 44, may be defined as one or more slits, holes, etc. having any of a variety of cross-sectional shapes or profiles as may be desired.

The inflation fluid 34 may be any of a variety of inflation mediums such as saline (with or without additional therapeutic agents), lactated ringers, etc. In at least one embodiment the fluid is a liquid. In at least one embodiment the inflation fluid 34 is also characterized as a coolant, having been cooled to, or having an inherent temperature of about 37 degrees Celsius or less. In at least one embodiment fluid 34 has a temperature of about 33 degrees Celsius to about 36 degrees Celsius.

When the fluid/coolant 34 is passed into the balloon interior 32 and more significantly directly by outflowing into the vessel 36 via openings 44, the fluid will provide a cooling effect to the surrounding tissues of the vessel 36. This cooling effect will help to reduce necrosis of the vessel tissue when blood flow is restored such as by reopening the vessel by expansion of the balloon 20 and/or placement of a stent 38.

In some embodiments the fluid 34 comprises a therapeutic agent which may be passed into the vessel 36 to treat the surrounding tissues as well as provide the cooling affect previously mentioned.

In some cases a therapeutic agent may be placed in the balloon interior or inflation lumen in the form of a coating that reacts with or is picked up by the fluid 34 as it flows therethrough. Such an agent may be in the form of a coating that may also be or alternatively placed on the balloon exterior and/or the stent. In at least one embodiment such a coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

While the openings 44 are configured to allow the fluid 34 to pass out of the balloon 20 when pressurized it is preferable that the openings 44 minimize or prevent back flow of fluids, such as blood, from entering the balloon interior 32 from the vessel 36 during the application of negative pressure during collapse/refold of the balloon prior to withdrawal of the catheter 10 from the vessel 36.

In some embodiments of the invention, the openings 44 may be provided with valves, baffles, barriers and/or other mechanisms which permit outflow of the fluid 34 while preventing backflow of the fluid or other bodily fluids.

In at least one embodiment the fluid 34 has a predetermined viscosity that is less than the viscosity of the blood and/or other fluids typically present in the vessel 36. The openings are then sized to allow passage of a fluid having a viscosity substantially equal or less than that of the fluid 34 but not fluids having a greater viscosity than the fluid 34. In at least one embodiment the openings are sized and/or configured to allow fluids having a viscosity similar to that of water and/or saline to pass therethrough, or approximately 1-2 centipoises. In some embodiments the openings 44 are about 8 microns to about 75 microns in area.

Figure 2:
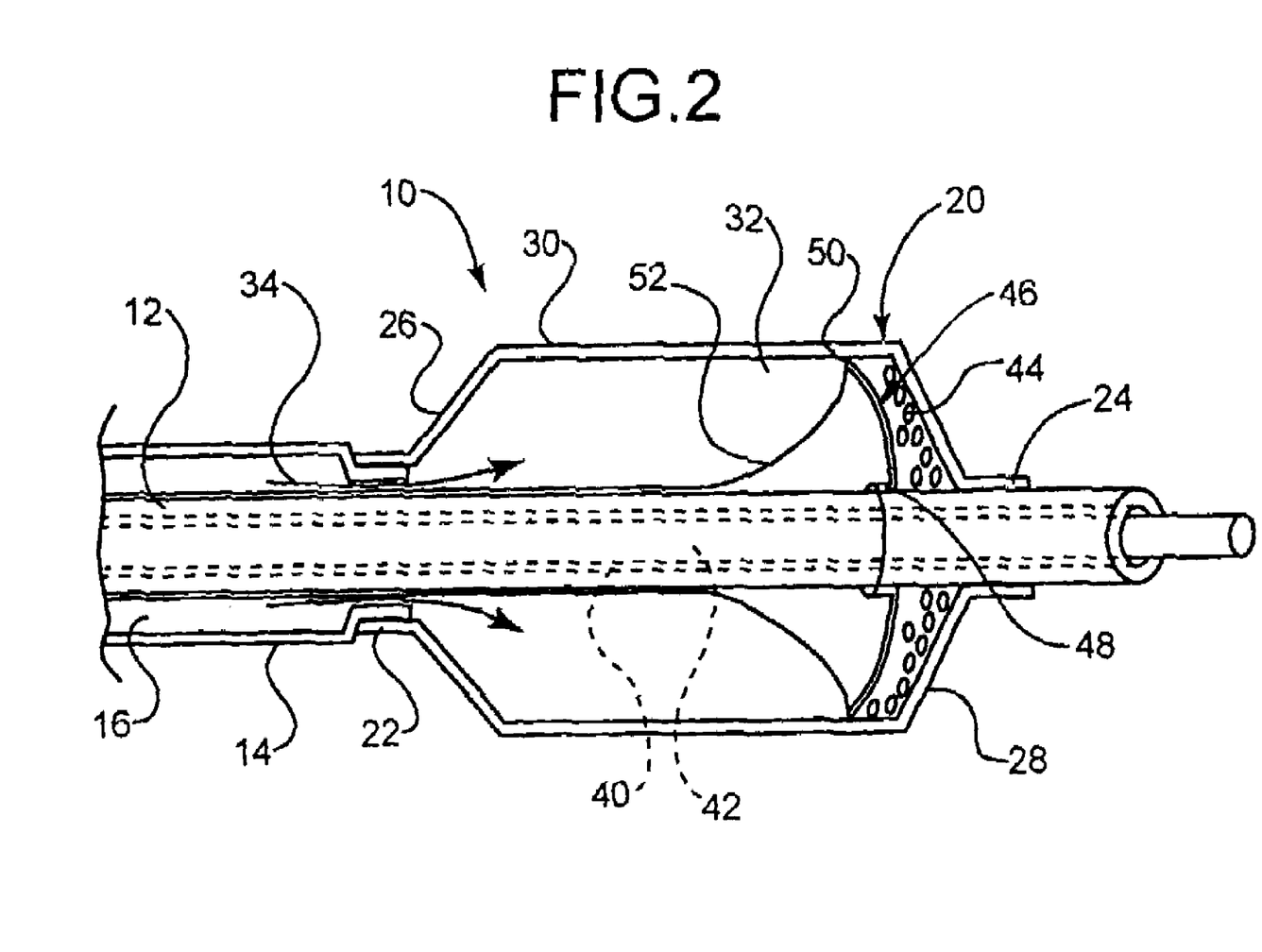
FIG. 2 is a partial cross-sectional side view of the embodiment shown in FIG. 1 including an interior occluding member.
Figure 3:
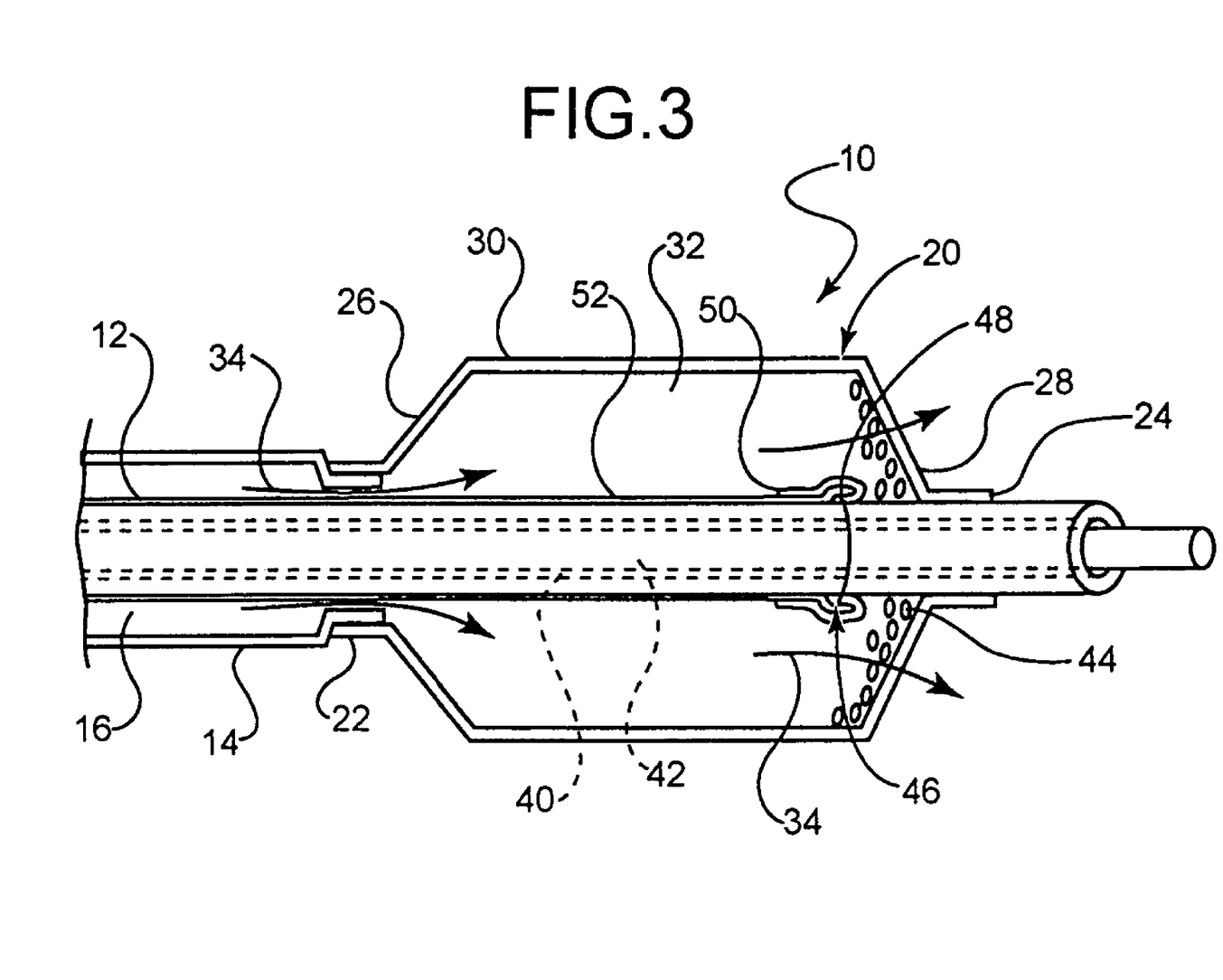
FIG. 3 is a partial cross-sectional side view of the embodiment shown in FIG. 2 wherein the occluding member is shown collapsed.

In at least one embodiment, an example of which is shown in FIGS. 2 and 3, the catheter 10 further comprises an occluding member 46 which is actuatable between a collapsed position shown in FIG. 3 and an occluding position shown in FIG. 2. In at least one embodiment the occluding member is a substantially cone-shaped member of flexible material such as polyurethane, SIBS, silicone, Pebax, etc. The occluding member 46 has a narrow end region 48 and a wider end region 50. The narrow end region 48 defines an inner diameter substantially the same as that of the inner shaft 12. In at least one embodiment the narrow end region 48 is bonded, welded, or otherwise engaged to the inner shaft 12 to effectively fix the end region 48 in place about the inner shaft 14.

When allowed to expand, the wider end region 50 defines an outside diameter sufficient to expand over and substantially cover the region of the distal cone 28 which includes the openings 44. In the embodiment show in FIG. 2 the wider end region 50 has an outer diameter which is substantially equal to the expanded inside diameter of the balloon 20.

When the occluding member 46 is in the expanded state shown in FIG. 2, the distal cone 28 is occluded from the rest of the balloon interior 32. As a result, the flow of fluid 34 to the openings 44 is reduced or eliminated. By varying the expansion and size of the occluding member 46 the flow rate of the fluid 34 to and through the openings 44 may be regulated as desired.

Several devices may be utilized with the catheter 10 to provide a mechanism for manipulating the position of the occluding member from the occluding position shown in FIG. 2 and the collapsed position shown in FIG. 3. For example, a tubular member disposed about the inner shaft 12 and moveable relative thereto, a plurality of actuation wires or other elongate member(s) 52 may be connected to the occluding member 46 which extend to the proximal end of the catheter (not shown). By pulling the members 52 proximally relative the inners shaft 12 the occluding member 46 may be pulled toward or into the collapsed position shown in FIG. 3. Conversely, by advancing the members 52 distally relative to the inner shaft 12 the wider end region 50 of the occluding member 46 may be expanded to occlude the distal cone 28 of the balloon 20.

In at least one embodiment the occluding member 46 is provided with a bellows which may be configured to elongate down against the inner shaft 12 when the occluding member 46 is in the collapsed state.

Figure 4:
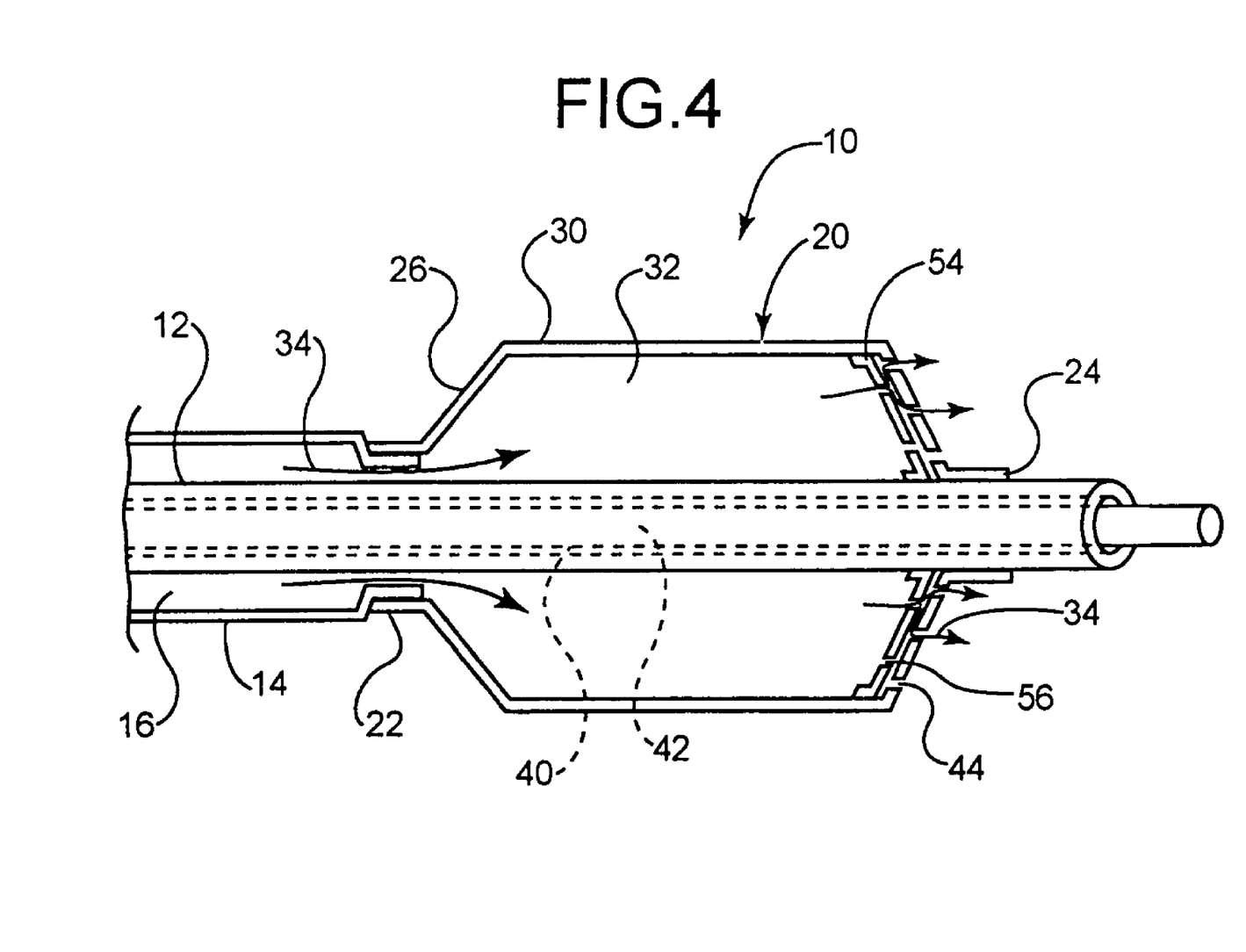
FIG. 4 is a partial cross-sectional side view of the embodiment shown in FIG. 1 including an interior baffle.

In at least one embodiment, an example of which is shown in FIG. 4, the catheter 10 comprises a baffle 54, which is positioned within the interior 32 of the balloon 20, proximally adjacent to the distal cone 28. In some embodiments the baffle 54 may be positioned distally external of the distal cone 28. The baffle 54 is an annular ring or other member which is disposed about the inner shaft 12, and which extends radially outward to engaged the balloon 20 thereby ensuring that its position within the balloon interior is maintained regardless of the inflation characteristics of the balloon. The baffle 54 is constructed of a flexible material which is be capable of some degree of expansion and flexing to accommodate the change in balloon shape and size during expansion.

The baffle 54 defines one or more baffle openings 56 therethrough. Each baffle opening 54 is positioned on the baffle 54 in such a way so that a given baffle opening 56 is longitudinally and/or radially offset from a distally adjacent balloon opening 44. As a result of this offset positioning diffusion of the fluid 34 being pushed out of the balloon openings 44 is improved. Furthermore, when applying negative pressure to the balloon 20 during balloon deflation, the offset nature of the openings 44 and 56 will allow the distal cone 28 and baffle 54 to have a tendency to occlude the respective openings therethrough, as the baffle 54 will tend to occlude the balloon openings 44 while the distal cone 28 will tend to occlude the baffle openings 54 as the distal cone 28 collapses against the baffle 54. The baffle 54 may be constructed of any of a variety of suitable materials including but not limited to: polyurethanes, Polyether block polyamide copolymers (PEBA), SIBS, silicone, polyesters, polyethers, etc.

Figure 5:
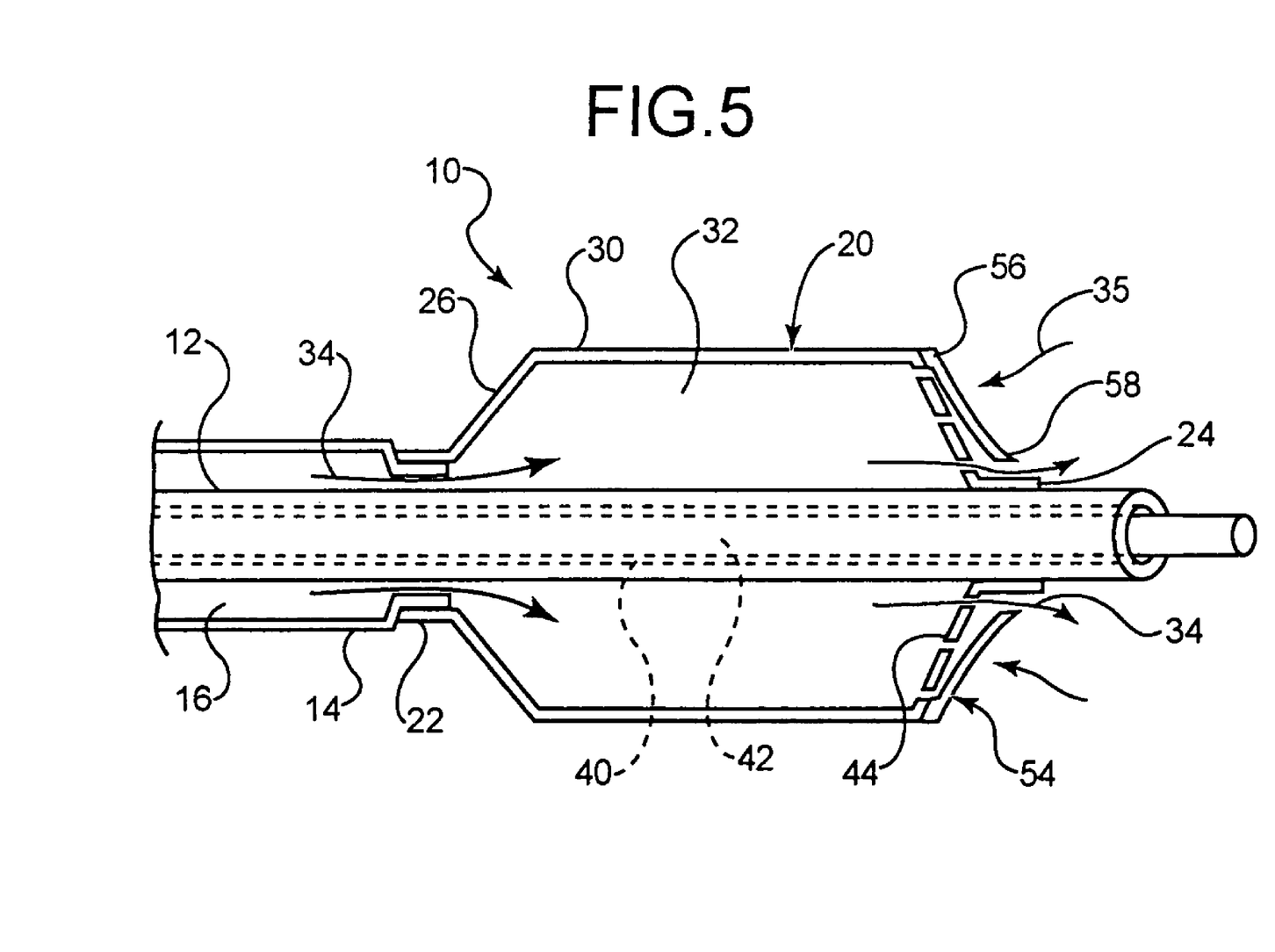
FIG. 5 is a partial cross-sectional side view of the embodiment shown in FIG. 1 including an exterior baffle engaged at one end to the balloon.
Figure 6:
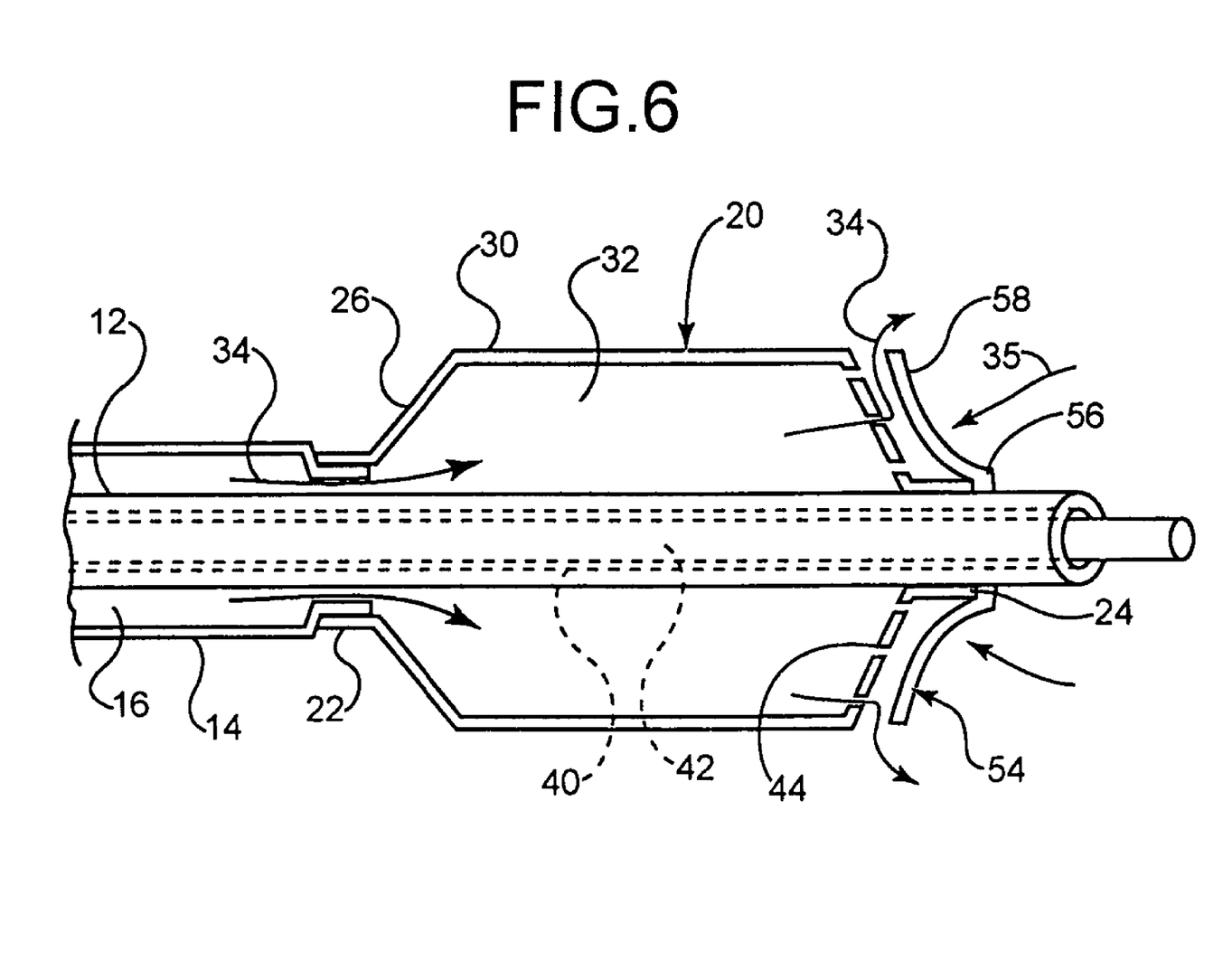
FIG. 6 is a partial cross-sectional side view of the embodiment shown in FIG. 1 including an exterior baffle engaged at one end to the inner shaft.

In some embodiments a baffle 54 may be provided external of the balloon 20, such as in the examples shown in FIGS. 5 and 6. Like the interior baffle depicted in FIG. 4, an externally mounted baffle may define one or more baffle openings therethrough. However, in the embodiments shown in FIGS. 5 and 6 rather than define openings through the material of the baffle 54, the baffle 54 is fixedly engaged along only one end region 56 to the balloon 20 (in the embodiment depicted in FIG. 5) and/or to the inner shaft 12 (in the embodiment depicted in FIG. 6).

By providing the catheter 10 with an external baffle 54 which is engaged to balloon 20 or shaft 12 in this manner, the baffle acts as a one way flap or valve, which permits the exit of fluid 34 from the balloon interior 32, but which limits or prevents entrance of bodily fluid such as blood, indicated by arrow 35, from entering the balloon during deflation. When the balloon 20 is expanded by injecting fluid 34 into the interior 32 of the balloon via lumen 16, the pressure is sufficient to expand the balloon and also eject some fluid 34 from the balloon through the openings 44. The pressure exerted by the fluid 34 against the baffle 54 is sufficient to lift the free end 58 of the baffle off of the distal cone 28 to allow the fluid 34 to pass out of the catheter 10. During deflation of the balloon 20, negative pressure is applied to the balloon, such as by vacuum through the lumen 16. Such a negative pressure will tend to pull the free end 58 of the baffle 54 against the distal cone 28, thereby forming a fluid tight seal over the openings 44.

In some embodiments the catheter 10 may be configured to avoid the use of openings in the balloon 20 to permit flow of fluid 34 distally out of the catheter. For example, in the embodiment shown in FIG. 7, the balloon interior 32 is in fluid communication with the guidewire lumen 40 through one or more openings or entrance ports 60 through the inner shaft 12. Thus a fluid path is provided, which allows fluid 34 which is transmitted through the inflation lumen 16 and into the balloon interior 32 to pass through the shaft entrance port 60 and into the guidewire lumen 40.

Figure 7:
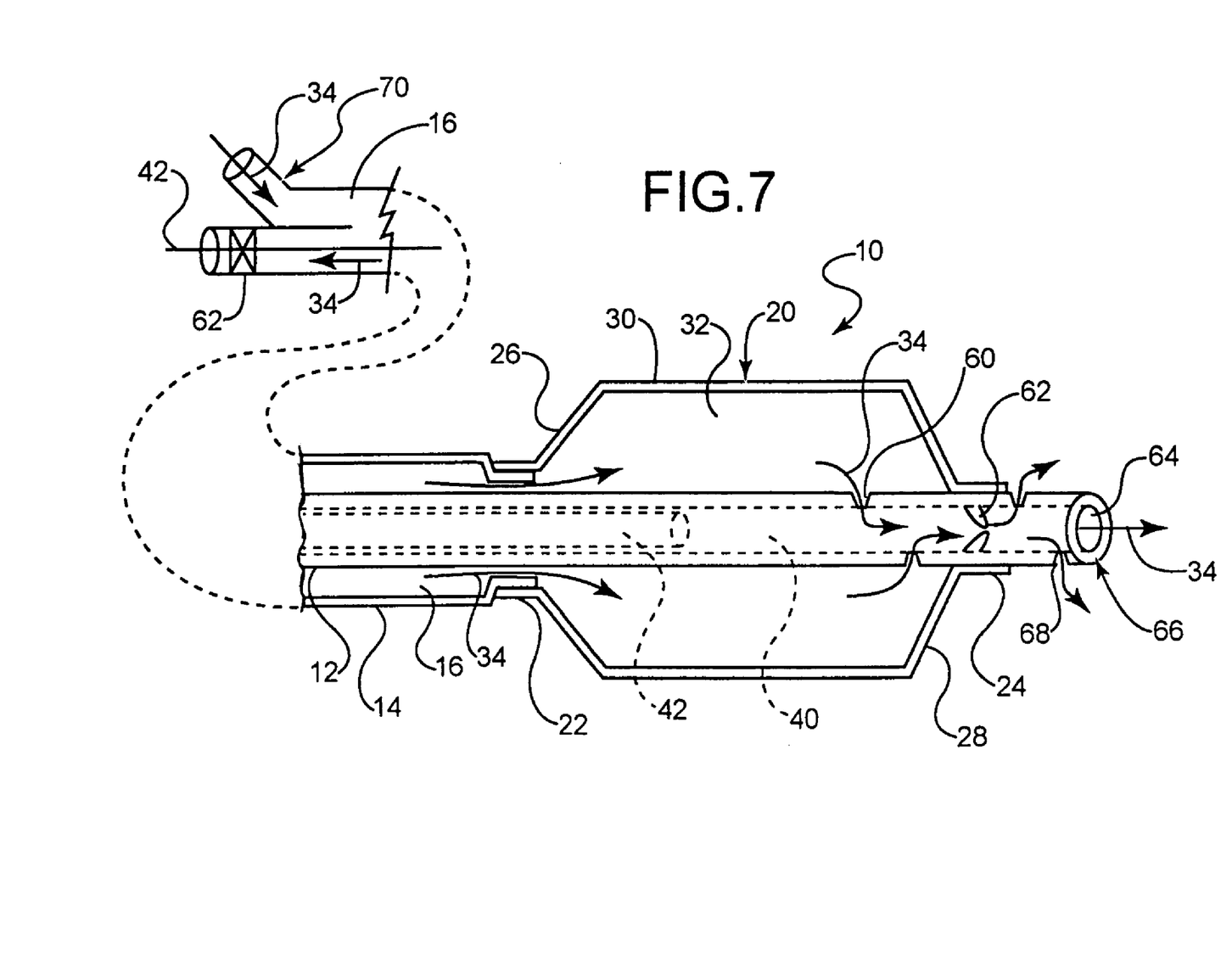
FIG. 7 is a partial cross-sectional side view of an embodiment of the invention wherein the guidewire lumen is in fluid communication with the balloon interior/inflation lumen.

The guidewire lumen 40 and/or the guidewire 42 may be sized or otherwise configured to prevent and/or limit the flow of fluid 34 from entering the lumen 40 while the guidewire 42 is positioned across the port 60. By withdrawing the guidewire 42 proximally to unblock the port 60 the fluid 34 is free to enter the guidewire lumen 40.

Once the fluid 34 is in the guidewire lumen 40 the fluid 34 is able to travel through the lumen 40 and out the opening 64 at the distal end 66 of the inner shaft 12. In some embodiments a valve mechanism may be positioned in the distal portion to prevent fluid from entering the lumen 40.

In some embodiments the inner shaft defines at least one exit port 68 through which the fluid 34 may exit the guidewire lumen 40. One or more exit ports 68 may be provided to alter the diffusion and/or direct the fluid 34 as it leaves the catheter 10.

In many catheter assemblies the guidewire lumen is typically open at both the distal end and proximal end of the catheter to allow the guidewire to pass freely therethrough. However, because the guidewire lumen 40 in this case is configured to transmit fluid 34 therethrough, the lumen at one or more points may include one or more valves, flaps, regulators or other flow regulating devices, herein after referred to collectively as valve mechanism(s) and depicted by reference numeral 62, which allow the guidewire 42 to pass therethrough but which provide a fluid seal in at least one direction to the lumen 40. For example, in at least one embodiment at the proximal end portion 70 of the lumen 40 a valve mechanism 62 may be provided which acts as a fluid static valve to prevent fluid 34 from exiting the catheter proximally therethrough, but which allows the guidewire 42 to freely pass. Additionally or alternatively, a one way valve mechanism 62 may be provided distal of the shaft entrance port 60 which is configured to permit the outflow of fluid 34 but prevents and/or limits bodily fluid such as blood from entering the balloon during deflation.

Figure 8:
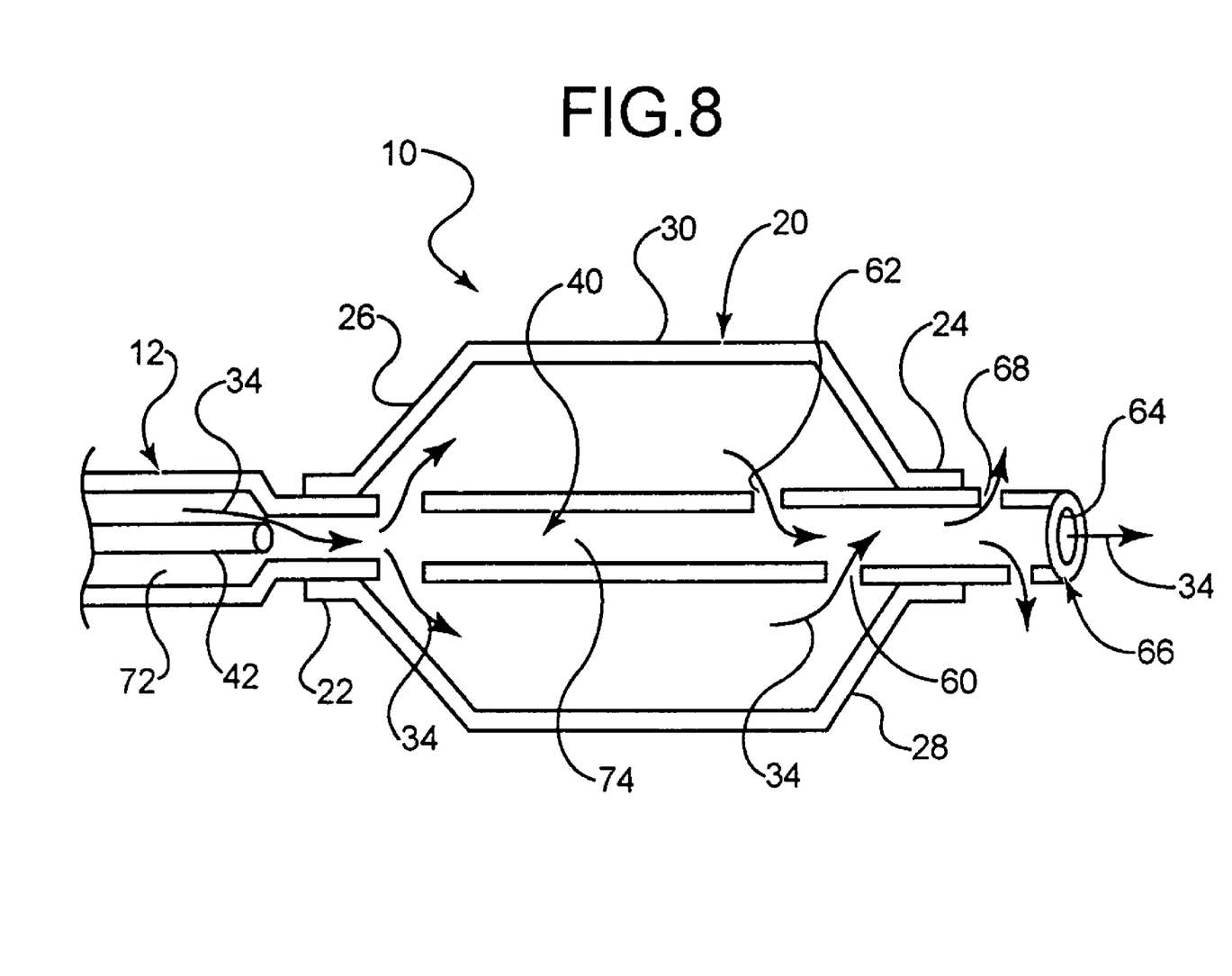
FIG. 8 is a partial cross-sectional side view of an embodiment of the invention wherein the balloon is mounted to a single catheter shaft.

In at least one embodiment, an example of which is shown in FIG. 8, the catheter 10 comprises a single shaft 12, similar in configuration to the inner shaft previously described in FIG. 7, about which the balloon 20 is mounted. The single shaft 12 includes one or more shaft entrance ports 60 and exit ports 68 to allow the balloon interior 32 and the guidewire lumen 40 to be in fluid communication such as in the manner described above. The shaft 12, and more significantly the guidewire lumen 40 defined by the shaft have a proximal portion 72 and a distal portion 74.

The proximal portion 72 is configured so that the inner diameter of the shaft 12 (i.e. guidewire lumen 40) is greater than the inner diameter of the distal portion 74. In at least one embodiment the distal portion 74 has an inner diameter of about 0.015 inches to about 0.020 inches, whereas the proximal portion 72 has a greater inner diameter of about 0.028 inches to about 0.032 inches. In at least one embodiment the inner diameter of the distal portion 74 is about 0.017 inches.

The proximal portion 72 is sized, such that when the guidewire 42 is present within the proximal portion 72 of the lumen 40 a space is maintained between the shaft 12 and the guidewire 42 which also functions to provide a lumen through which the fluid 34 may be transported.

The guidewire 42 and the distal portion 74 of the lumen 40 are of a complementary diameter size, which is less than that of the proximal portion 72, such that when the guidewire 42 is passed into the distal portion 74 of the guidewire lumen 40, there is insufficient space to provide adequate flow of the fluid into the distal portion 74. By removing the guidewire proximally from the distal portion 74, the distal portion of the lumen 40 becomes unobstructed to the flow of fluid 34 as depicted in FIG. 8. In some embodiments a valve mechanism may be provided distally of the fluid entrance port 60, within or external to the lumen 40 to regulate pressure in the balloon interior 32 and flow of the fluid 34 out of the catheter 10.

In the various embodiments discussed thus far, the catheter 10 employs a fluid 34 which acts to inflate the balloon 20 as well as act as an infusate or coolant medium that is diffused distally out of the catheter 10. As indicated above, however configurations of the catheter 10 which accommodate a single inflation/infusate fluid 34 may require the use of various ports, valve mechanisms and/or other devices such as baffles to properly diffuse the fluid and to prevent backflow of bodily fluids during balloon collapse. In some embodiments however, the catheter may be configured with an inflation lumen which is separate and distinct from an infusate or coolant lumen. These embodiments may avoid the need for many of the flow regulating mechanisms previously described.

Figure 9:
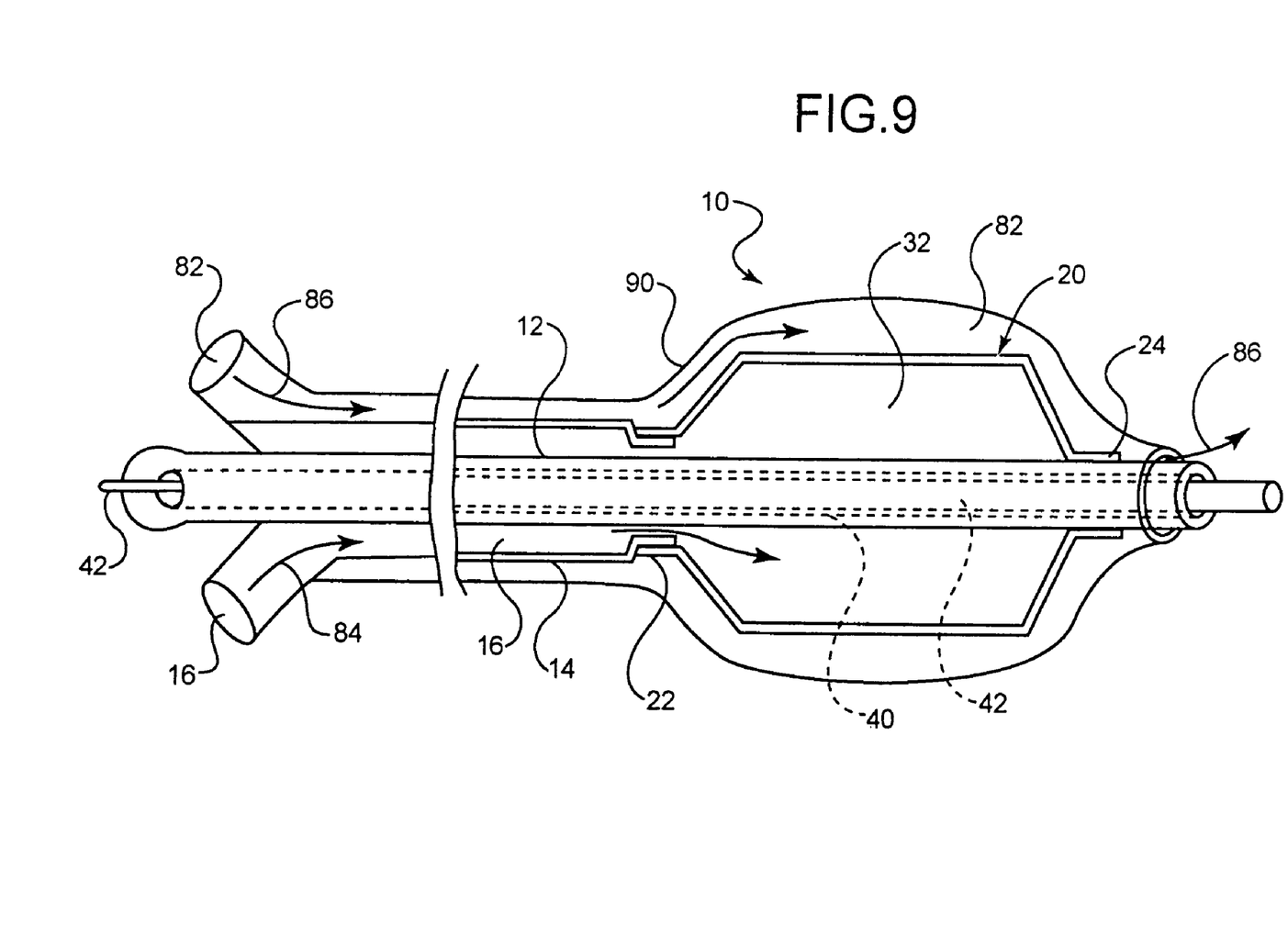
FIG. 9 is a partial cross-sectional side view of an embodiment of the invention wherein a separate infusion member is disposed about the balloon.

In at least one other embodiment, an example of which is illustrated in FIG. 9, the catheter 10, may have the balloon mounting configuration using an inner shaft 12 distally and an outer shaft 14 proximally, such as that previously shown and described in FIG. 1. However, the catheter 10 shown in FIG. 9 also includes an outer sheath 90. The outer sheath 90 effectively forms the outer perimeter of a dedicated and separate infusate lumen 82 whereas, moving proximally to distally, the outer shaft 14, the balloon 20 and optionally the inner shaft 12 defines the inner perimeter of the infusate lumen 82.

The addition of the sheath 90 may be used on a wide variety of existing catheter assemblies to provide the catheter with a coolant delivery mechanism.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
    a catheter, the catheter having at least one catheter shaft, the at least one catheter shaft defining an inflation lumen for transport of an inflation fluid therethrough, the inflation fluid comprising a coolant;
    an expandable balloon, the balloon having a proximal cone, a distal cone and a body region therebetween, the balloon being engaged to a distal region of the at least one catheter shaft, the balloon defining an exterior and an interior, the interior being in fluid communication with the inflation lumen, a portion of the catheter shaft distal of the balloon defining at least one shaft exit port and a portion of the catheter shaft within the balloon defining at least one port in fluid communication with the inflation lumen and the balloon interior;
    a baffle positioned on the balloon interior proximal to the distal cone and disposed about said at least one catheter shaft, the baffle extending radially outward from said shaft to engage said balloon, the baffle further defining one or more baffle openings therethrough, the one or more baffle opening longitudinally or radially offset from a distally adjacent balloon opening;
    wherein the baffle is constructed and arranged to permit the exit of fluid from the balloon interior through the plurality of ports to the balloon exterior but limit the entrance of bodily fluid from entering the balloon interior from the balloon exterior during deflation.

2. The medical device of claim 1 wherein the baffle is actuatable from a collapsed state to an occluded state, in the occluded state the baffle at least partially occluding the plurality of ports.

3. The medical device of claim 2 wherein a first end portion of the baffle being engaged to the at least one catheter shaft, a second end portion of the baffle being moveable relative to the at least one catheter shaft.

4. The medical device of claim 3 wherein the second end portion is operatively engaged to at least one actuation member, the at least one actuation member extending proximally along the at least one catheter shaft and is moveable relative thereto, such that moving the at least one actuation member in a distal direction actuates the baffle from the collapsed state to the occluded state, and moving the at least one actuation member in the proximal direction actuates the baffle from the occluded state to the collapsed state.

5. The medical device of claim 4 wherein the actuation member is a bellows.

6. The medical device of claim 1 wherein a first end portion of the baffle is fixedly engaged to the catheter and a second end portion of the baffle is moveable relative to the catheter.

7. The medical device of claim 6 wherein the first end portion of the baffle is engaged to the balloon.

8. The medical device of claim 1 wherein the baffle is positioned adjacent to the distal cone of the balloon, wherein the baffle comprises a first end portion and a second end portion, the first end portion of the baffle being engaged to at least a portion the distal cone and the second end portion being engaged to the at least one catheter shaft, the baffle defining a plurality of baffle openings therethrough.

9. The medical device of claim 8 wherein each of the plurality of ports is radially offset from each of the plurality of baffle openings.

10. The medical device of claim 1 wherein the catheter comprises at least one valve mechanism.

11. The medical device of claim 10 wherein the at least one valve mechanism is positioned in the inflation lumen.

12. The medical device of claim 11 wherein the at least one valve mechanism permits the inflation fluid to flow freely through the inflation lumen in only one direction.

13. The medical device of claim 10 wherein the at least one valve mechanism permits the inflation fluid to flow freely through the at least one port in only one direction.

14. The medical device of claim 1 wherein the at least one catheter shaft comprises an inner shaft and an outer shaft, the outer shaft disposed about a proximal portion of the inner shaft, a distal portion of the inner shaft extending distally therefrom;

the balloon further comprises a proximal waist proximal of the proximal cone and a distal waist distal of the distal cone, the proximal waist being engaged to the outer shaft, the distal waist being engaged to the distal portion of the inner shaft, the inflation lumen being defined by the proximal portion of the inner shaft and the outer shaft disposed thereabout.

15. The medical device of claim 14 wherein the inner shaft defines a guidewire lumen for passage of a guidewire therethrough.

16. The medical device of claim 1 further comprising a guidewire, the guidewire having a guidewire diameter, the guidewire moveable through the inflation lumen.

17. The medical device of claim 16 wherein the inflation lumen comprises a proximal portion and a distal portion, the proximal portion having a diameter greater than that of the distal portion, the distal portion having a diameter approximately the same as the guidewire diameter.

18. The medical device of claim 17 wherein the distal region of the at least one catheter shaft which underlies the balloon defines at least one shaft entrance port, which provides the fluid communication between the balloon interior and the inflation lumen.

19. The medical device of claim 18 wherein the at least one shaft distal of the balloon defines at least one shaft exit port, which provides fluid communication between the inflation lumen and the balloon exterior.

20. The medical device of claim 1 wherein the coolant has a temperature of about 37 degrees Celsius or less.

21. The medical device of claim 1 wherein the inflation fluid is selected from at least one member of the group consisting of: saline, Ringers Lactate, a therapeutic agent and any combinations thereof 22. The medical device of claim 1 wherein the inflation fluid comprises at least one therapeutic agent.

23. The medical device of claim 1 further comprising an expandable stent, prior to expansion the stent being disposed about at least a portion of the body region of the balloon.

24. The medical device of claim 23 further comprising at least one therapeutic agent applied thereto.

25. The medical device of claim 24 wherein the at least one therapeutic agent is a coating, the coating being applied to at least one surface selected from the group consisting of a surface of the balloon, a surface of the stent and any combination thereof 26. The medical device of claim 24 wherein the at least one therapeutic agent selected from at least one member of the group consisting of: at least one non-genetic therapeutic agent, at least one genetic therapeutic agent, at least one type of cellular material, and any combination thereof 27. The medical device of claim 24 wherein the at least one therapeutic agent comprises at least one polymer agent.

28. A medical device comprising:
a catheter, the catheter having at least one catheter shaft, the at least one catheter shaft defining an inflation lumen for transport of an inflation fluid therethrough, the inflation fluid comprising a coolant;
an expandable balloon, the balloon having a proximal cone, a distal cone and a body region therebetween, the distal cone defining a plurality of ports, the balloon being engaged to a distal region of the at least one catheter shaft, the balloon defining an exterior and an interior, the interior being in fluid communication with the inflation lumen, a portion of the catheter distal of the balloon body defining at least one port in fluid communication with the inflation lumen and the balloon interior;
a flexible baffle disposed about the at least one catheter shaft, a first end portion of the baffle being engaged to the at least one catheter shaft and a second end portion of the baffle being moveable relative to the at least one catheter shaft, the baffle actuatable from a collapsed state to an occluded state, the baffle positioned in the balloon interior adjacent to the distal cone, the baffle constructed and arrange to permit the inflation fluid to pass from the balloon interior, through the plurality of ports, to the balloon exterior and to limit flow from the balloon exterior to the balloon interior, in the occluded state, the baffle at least partially occluding the plurality of ports; and
at least one actuation member, the second end portion of the baffle operatively engaged to the at least one actuation member, the at least one actuation member extending proximally along the at least one catheter shaft and is moveable relative thereto, such that moving the at least one actuation member in a distal direction actuates the baffle from the collapsed state to the occluded state, and moving the at least one actuation member in the proximal direction actuates the baffle from the occluded state to the collapsed state.

29. A medical device comprising:
a catheter, the catheter having at least one catheter shaft, the at least one catheter shaft defining an inflation lumen for transport of an inflation fluid therethrough, the inflation fluid comprising a coolant;
an expandable balloon, the balloon having a proximal cone, a distal cone and a body region therebetween, the balloon being engaged to a distal region of the at least one catheter shaft, the balloon defining an exterior and an interior, the interior being in fluid communication with the inflation lumen, a portion of the catheter shaft distal of the balloon defining at least one shaft exit port and a portion of the catheter shaft within the balloon defining at least one port in fluid communication with the inflation lumen and the balloon interior;
a baffle positioned on the balloon interior proximal to the distal cone and disposed about the catheter shaft, the baffle having a first end portion being engaged to the at least one catheter shaft and a second end portion being moveable relative to the at least one catheter shaft, the baffle including a plurality of ports, the baffle is constructed and arranged to permit the exit of fluid from the balloon interior through the plurality of ports to the balloon exterior but limit the entrance of bodily fluid from entering the balloon interior from the balloon exterior during deflation; and
an actuation member, the at least one actuation member extending proximally along the at least one catheter shaft and is moveable relative thereto;
wherein the baffle is actuatable from a collapsed state to an occluded state, in the occluded state the baffle at least partially occluding the plurality of ports wherein the second end portion is operatively engaged to at least one actuation member, such that moving the at least one actuation member in a distal direction actuates the baffle from the collapsed state to the occluded state, and moving the at least one actuation member in the proximal direction actuates the baffle from the occluded state to the collapsed state.

\* \* \* \* \*